United States Patent
Steinhauer et al.

(10) Patent No.: US 11,183,287 B2
(45) Date of Patent: Nov. 23, 2021

(54) ANALYTICS REGARDING PATIENT CARE

(71) Applicant: CareFusion 303, Inc., San Diego, CA (US)

(72) Inventors: Tom Steinhauer, San Diego, CA (US); Terry Lee Blansfield, Orange, CA (US); Leonard Mulkowsky, Del Mar, CA (US); Andres Jesus Calderon, III, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 14/099,773

(22) Filed: Dec. 6, 2013

(65) Prior Publication Data

US 2014/0371543 A1 Dec. 18, 2014

Related U.S. Application Data

(63) Continuation-in-part of application No. 13/917,614, filed on Jun. 13, 2013.

(51) Int. Cl.
*G16H 20/17* (2018.01)
*A61M 5/168* (2006.01)
(Continued)

(52) U.S. Cl.
CPC ............ *G16H 20/17* (2018.01); *A61M 5/142* (2013.01); *A61M 5/16831* (2013.01);
(Continued)

(58) Field of Classification Search
CPC ...... G06Q 50/22; G06Q 50/24; G06F 19/322; G06F 19/323–327
(Continued)

(56) References Cited

U.S. PATENT DOCUMENTS 4,346,101 A   8/1982   Lednicer
4,551,133 A * 11/1985   Beyl ................... A61M 5/1723
                                                        604/66
(Continued)

FOREIGN PATENT DOCUMENTS

CN   1493049 A   4/2004
CN   1759398 A   4/2006
(Continued)

OTHER PUBLICATIONS

Happ et al., Wash and Wean: Bathing Patients Undergoing Weaning Trials During Prolonged Mechanical Ventilation, Heart Lung. 2010; 39(6 Suppl), 16 pages.*

(Continued)

*Primary Examiner* — Jason S Tiedeman
(74) *Attorney, Agent, or Firm* — Morgan, Lewis & Bockius LLP

(57) ABSTRACT

A method, system and computer-readable medium are provided for determining compliance with patient care protocols, comprising an infusion pump providing infusion information pertaining to one or more drugs administered to a patient, the one or more drugs including sedatives and analgesics, and a processor communicably coupled to the infusion pump and configured to determine information regarding the one or more drugs being administered to the patient based on the infusion information by determining a baseline threshold for the one or more drugs being administered to the patient according to the actual dosage of the one or more drugs administered to the patient prior to a current time, determining a dosage amount of the one or more drugs currently being administered to the patient and comparing the dosage amount of the one or more drugs currently being administered to the baseline threshold to determine a deviation from the baseline threshold.

20 Claims, 7 Drawing Sheets

(51) Int. Cl.
| | | |
|---|---|---|
| *A61M 5/142* | (2006.01) | |
| *A61B 5/00* | (2006.01) | |
| *A61M 16/00* | (2006.01) | |

(52) U.S. Cl.
CPC ............ *A61B 5/4821* (2013.01); *A61B 5/4848* (2013.01); *A61B 2505/03* (2013.01); *A61M 16/0051* (2013.01); *A61M 16/021* (2017.08); *A61M 2005/14208* (2013.01)

(58) Field of Classification Search
USPC ........................................................ 705/2, 3
See application file for complete search history.

(56) References Cited

U.S. PATENT DOCUMENTS

| | | | | |
|---|---|---|---|---|
| 5,069,668 | A * | 12/1991 | Boydman | A61M 5/172 604/121 |
| 5,681,285 | A * | 10/1997 | Ford | G06F 15/025 604/151 |
| 5,781,442 | A * | 7/1998 | Engleson | G16H 40/67 700/214 |
| 6,148,814 | A * | 11/2000 | Clemmer | A61M 16/024 128/200.24 |
| 6,273,088 | B1 * | 8/2001 | Hillsman | A61M 16/0051 128/204.23 |
| 8,862,196 | B2 * | 10/2014 | Lynn | A61B 7/003 600/323 |
| 9,031,793 | B2 * | 5/2015 | Lynn | G16H 20/17 702/19 |
| 9,295,840 | B1 * | 3/2016 | Thacker | A61N 1/36128 |
| 2003/0135087 | A1 | 7/2003 | Hickle | |
| 2004/0128162 | A1 | 7/2004 | Schlotterbeck et al. | |
| 2004/0129271 | A1 * | 7/2004 | Hickle | G06F 19/3406 128/204.23 |
| 2005/0177400 | A1 | 8/2005 | Rosenfield | |
| 2006/0247489 | A1 * | 11/2006 | Carbis | A61M 21/00 600/27 |
| 2007/0067186 | A1 * | 3/2007 | Brenner | G06Q 50/22 705/2 |
| 2007/0257788 | A1 | 11/2007 | Carlson et al. | |
| 2008/0201325 | A1 | 8/2008 | Doniger et al. | |
| 2009/0164249 | A1 | 6/2009 | Hunt | |
| 2009/0177181 | A1 | 7/2009 | Schmidt | |
| 2010/0121170 | A1 | 5/2010 | Rule | |
| 2010/0121654 | A1 | 5/2010 | Portnoy et al. | |
| 2010/0198622 | A1 | 8/2010 | Gajic | |
| 2010/0261977 | A1 | 10/2010 | Seely | |
| 2010/0268157 | A1 | 10/2010 | Wehba et al. | |
| 2010/0324936 | A1 * | 12/2010 | Vishnubhatla | G06F 19/322 705/3 |
| 2011/0078608 | A1 | 3/2011 | Gannon et al. | |
| 2011/0082440 | A1 * | 4/2011 | Kimmo et al. | 604/503 |
| 2011/0184303 | A1 | 7/2011 | Skinner et al. | |
| 2011/0213215 | A1 | 9/2011 | Doyle | |
| 2011/0257798 | A1 | 10/2011 | Ali et al. | |
| 2011/0313789 | A1 * | 12/2011 | Kamen | G16H 10/65 705/3 |
| 2012/0041279 | A1 | 2/2012 | Freeman et al. | |
| 2012/0323212 | A1 * | 12/2012 | Murphy | G06F 3/0488 604/500 |
| 2013/0006075 | A1 | 1/2013 | Baker | |
| 2013/0199533 | A1 | 8/2013 | Steinhauer | |
| 2014/0002246 | A1 | 1/2014 | Steinhauer | |
| 2014/0060540 | A1 | 3/2014 | Milne et al. | |
| 2014/0060541 | A1 | 3/2014 | Boyer et al. | |
| 2014/0114676 | A1 * | 4/2014 | Holmes | G06F 19/3456 705/2 |
| 2014/0150796 | A1 | 6/2014 | Milne | |
| 2014/0235959 | A1 | 8/2014 | Jafari et al. | |

FOREIGN PATENT DOCUMENTS

| | | | |
|---|---|---|---|
| EP | 2422695 A2 | 2/2012 | |
| EP | 2609855 A1 * | 7/2013 | ............... A61B 5/00 |
| JP | 2006512673 A | 4/2006 | |
| JP | 2007521849 A | 8/2007 | |
| JP | 2011200472 A | 10/2011 | |
| JP | 2012523895 A | 10/2012 | |
| JP | 2013543769 A | 12/2013 | |
| JP | 2014502854 A | 2/2014 | |
| RU | 2295361 C2 | 3/2007 | |
| RU | 2444281 C2 | 3/2012 | |
| WO | WO-2005050524 A2 | 6/2005 | |
| WO | WO-2005/072792 A1 * | 8/2005 | .............. A61M 5/00 |
| WO | WO 2005072792 A1 * | 8/2005 | .......... A61M 5/1723 |
| WO | WO-2009048462 A1 | 4/2009 | |
| WO | WO-2013/03953 A1 | 1/2013 | |
| WO | WO-2013/067223 A1 | 5/2013 | |
| WO | WO-2013067233 A1 | 5/2013 | |

OTHER PUBLICATIONS

Nathan Teuscher, Learn PK/PD, Training for the future, What is a half-life?, Dec. 20, 2010, 4 pages.*
Phyllis Maguire, "Wake Up and Breathe Protocol Cuts Patient Time on the Ventilator," Feb. 2008, http://www.todayshospitalist.com/index.php/index.php?b+articles_reas&cnt=511, 3 pages.
International Search Report and Written Opinion in International Application No. PCT/US2014/039597 dated Oct. 21, 2014, 13 pages.
International Search Report and Written Opinion for International Application No. PCT/US2014/068922, dated Apr. 2, 2015, 12 pages.
Girard, et al. "Efficacy and safety of a paired sedation and ventilator weaning protocol for mechanically ventilated patients in intensive care (Awakening and Breathing Controlled trial): a randomised controlled trial", Jan. 12, 2008, The Lancet, vol. 371, pp. 126-134.
Chinese Office Action for Application No. 2014800334975, dated Jun. 15, 2017, 10 pages excluding translation.
Chinese Office Action for Application No. 201480066337.0, dated Dec. 28, 2017, 11 pages excluding English translation.
Chinese Office Action for Application No. 201480066337.0, dated Oct. 15, 2018, 4 pages.
Japanese Office Action for Application No. 2016-519521, dated Oct. 18, 2018, 6 pages.
Japanese Office Action for Application No. 2016-535140, dated Oct. 17, 2018, 7 pages.
Chinese Office Action for Application No. 20480033497.5, dated May 2, 2018, 21 pages.
Japanese Office Action for Application No. 2016-519521, dated Mar. 2, 2018, 9 pages.
Russian Office Action for Application No. 2015155889, dated Mar. 19, 2018, 11 pages.
Duan, Z., et al., "Comparison Between SmartCare Weaning Mode and Traditional Weaning Mode in the Course of Mechanical Ventilation Weaning", J Clin Res, Sep. 2010, vol. 27, No. 9, pp. 1690-1692.
Russian Office Action for Application No. 2016127060, dated Jun. 25, 2018, 7 pages.
Australian Office Action for Application No. 2014278649, dated Feb. 11, 2019, 3 pages.
Chinese Office Action for Application No. 201480033497.5, dated Feb. 3, 2019, 4 pages.
Australian Office Action for Application No. 2014360182, dated May 24, 2019, 3 pages.
European Office Action for Application No. 14819220.6, dated Apr. 8, 2019, 6 pages.
European Office Action for Application No. 14819220.6, dated Jul. 2, 2020, 8 pages.
Japanese Office Action for Application No. 2019-132758, dated May 26, 2020, 7 pages.
Mexican Office Action for Application No. MX/a/2016/006549, dated Jul. 19, 2019, 6 pages.

(56) References Cited

OTHER PUBLICATIONS

Australian Office Action for Application No. 2014360182, dated Nov. 20, 2019, 4 pages.
Canadian Office Action for Application No. 2929708, dated Mar. 12, 2021, 5 pages.
Japanese Office Action for Application No. 2019132758, dated Mar. 18, 2021, 7 pages including translation.
Japan Office Action for Application No. 2016-519521, dated Feb. 26, 2020, 5 pages.
Japanese Office Action for Application No. 2016-519521, dated Dec. 1, 2020, 4 pages including translation.
India Office Action for Application No. 201637015736, dated Aug. 30, 2020, 8 pages.
India Office Action for Application No. 4208/KOLNP/2015, dated Sep. 23, 2020, 8 pages.
Japanese Office Action for Application No. 2019-132758, dated Oct. 23, 2020, 7 pages.
United Arab Emirates Office Action for Application No. P67172016, dated Jul. 11, 2021, 10 pages.

\* cited by examiner

ANALYTICS REGARDING PATIENT CARE

CROSS-REFERENCE TO RELATED APPLICATION

The present application is a continuation-in-part of U.S. patent application Ser. No. 13/917,614 entitled "Analytics Regarding Ventilated Patients," filed on Jun. 13, 2013, the disclosure of which is hereby incorporated by reference in its entirety for all purposes.

BACKGROUND

Field

The present disclosure generally relates to systems and methods facilitating optimization of patient care, and, in particular, relates to monitoring of patient sedation and pain therapy and the process of weaning ventilated patients off of the ventilator.

Description of the Related Art

Mechanical ventilator patients, who are intubated in a care facility, typically receive sedation and pain therapy from an infusion pump, as well as life-support from the mechanical ventilator device. Typically, a Nurse operates the infusion pump and has the overall responsibility for the patient. The ventilator is typically operated by a Respiratory Therapist.

The mechanical ventilator provides life support by assisting the patient with the inhalation of oxygen and the exhalation of $CO_2$ in order to maintain the necessary $PaO_2$, $PaCo_2$ and pH arterial blood levels, when the patient is unable to sustain adequate levels with their own spontaneous breathing. Positive pressure mechanical ventilators pump air with a controllable percentage of inspired oxygen (21%-100%) during the inspiratory phase of the breathing cycle. When the inspiratory phase of the breathing cycle is complete, the patient exhales through the ventilator by utilizing the natural recoil characteristics of the lungs. The volume of air that is introduced into the lungs on each cycle is the "tidal volume." This process is very invasive and introduces a high potential for complications such as baro trauma and secondary infections. Furthermore, the analgesics (or other pain medication) and sedatives commonly prescribed to such patients to provide patient comfort can themselves lead to adverse patient outcomes.

Thus, it is desirable to end the use of a mechanical ventilator as early as possible. Many of the rules and protocols for transitioning a patient off of a mechanical ventilator, or "weaning" the patient, include a series of clinical interventions including sedation and pain therapy management where the amount of sedatives and analgesics or other pain medications is reduced to awaken the patient and enable the return of their natural respiratory drive. "Spontaneous awakening trials" or "sedation vacations" where the patient is awakened as tolerated and monitored, and "spontaneous breathing trials" or "weaning trials" where the ventilator support is reduced or stopped for a period of time and the patient is monitored during the trial to identify signs of distress or difficulty. If the patient is able to successfully complete the prescribed weaning trials, "extubation" may be performed where the ventilator is removed, or the patient may be put back on full support to further prepare them for extubation.

Such interventions that facilitate a total dose reduction in analgesic and sedative medications such as the use of nurse controlled protocol guided sedation, the combination of spontaneous awakening and breathing trials, and the use of short acting medications, are associated with improved outcomes such as decreased time of mechanical ventilation and Intensive Care Unit (ICU) length of stay. Titration of individual patients' sedation throughout their ICU admission is also managed to reduce over-sedation and side-effects, and contributes to reduced duration of mechanical ventilation and length of stay.

SUMMARY

Certain aspects of the disclosed method facilitate managing rules and protocols for patient care. In certain embodiments, a method is provided for monitoring patient care. The method includes the steps of determining a baseline threshold for one or more medications being administered to a patient, the one or more medications including sedatives and pain therapy drugs, the baseline threshold being calculated from an actual dosage of the one or more medications administered to a patient prior to a current time, determining a dosage amount of the one or more medications currently being administered to a patient, comparing the dosage amount of the one or more medications currently being administered to the baseline threshold to determine a deviation from the baseline threshold and generating information regarding administration of medication to the patient according to the deviation from the baseline threshold.

In certain embodiments, a system for determining compliance with one or more patient care rules and protocols is provided. The system comprises an infusion pump providing infusion information pertaining to one or more drugs provided to a patient, wherein the one or more drugs include one or more sedatives and pain therapy drugs and a processor communicably coupled to the infusion pump and configured to determine information regarding the one or more drugs being administered to the patient based on the infusion information according to a set of rules and protocols regarding the preferred method of patient care for the patient, the rules and protocols including rules for administration of medication to the patient and generate analytics regarding patient care according to the determined information and the rules and protocols.

In certain embodiments, a non-transitory computer-readable medium having computer-executable instructions stored thereon for execution by a processor to perform a method of determining compliance with one or more patient care rules and protocols is provided. The method comprises the steps of receiving infusion information pertaining to one or more drugs provided to a patient, the one or more drugs including sedatives and pain therapy drugs, determining a set of patient care rules and protocols for the patient according to the type of patient and patient therapy being administered to the patient, determining a variation between the infusion information and the rules and protocols for the patient and providing one or more analytics at least in part based on the variation.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1A:
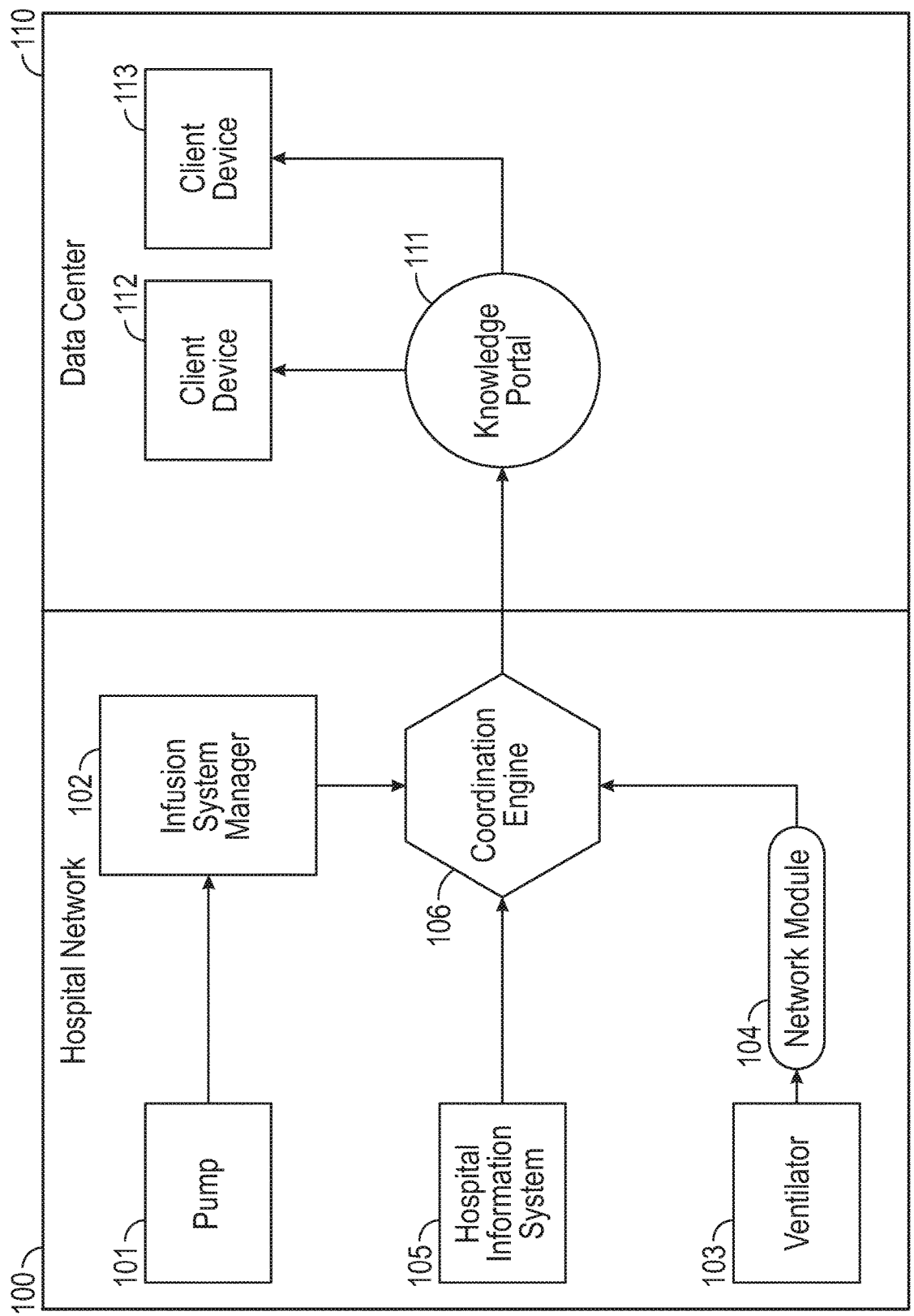
FIGS. 1A and 1B depict exemplary hospital networks for collecting patient information and facilitating management of rules and protocols for patients in accordance with aspects of the present disclosure.

The process of managing care of a patient, such as a ventilated patient, to ensure optimal levels of sedation and pain therapy and/or proper ventilation to minimize side effects of over sedation or prolonged ventilation is essential to reduce duration of mechanical ventilation and/or length of stay as well as the overall impact of patient care on the short term and long term patient condition. To facilitate managing of these concerns, many critical care facilities such as hospitals, ICUs, long term acute care ("LTAC") units, skilled nursing facility and/or other care facilities, may have one or more rules and protocols, such as best practice rule sets, sedation protocols, ventilation and weaning protocols and other similar guidelines, to guide nursing and medical staff. In one example, one or more patient care rules and protocols are defined and/or communicated according to best practice rule sets, predefined rules and protocols, and/or physician orders for providing care to patients (e.g., ventilated patients). As used herein, the phrase "rules and protocols" is used generally to refer to one or more orders (e.g., physician order), best practices, rules and/or protocols for providing care to patients. While various examples of the present disclosure are described with respect to a ventilated patient, it should be understood by one of ordinary skill in the art that the many of the methods, systems and processes described herein may be applied to an array of patients receiving care.

Because following patent care rules and protocols is intended to lead to optimal results in patient care, it is helpful to facilitate regular oversight of whether these rules and protocols are followed, and provide for management and updating of such rules and protocols. Typically such rules and protocols provide for a set of steps to be followed for each patient, including patients placed on a mechanical ventilator ("ventilated patient"), with respect to dosage and titration of sedatives and pain therapy medication (e.g., analgesics), timing and frequency of spontaneous awakening trials or sedation vacations ("SATs"), timing and criteria for performing spontaneous breathing trials ("SBTs") and/or timing and criteria for patient extubation when mechanical ventilation is terminated and the tube is removed from the patient.

These rules and protocols are usually put into place and/or communicated by physicians and/or care facility staff and supervisors to be followed by nurses and therapists. To provide for monitoring and improving compliance with such rules and protocols within a patient care facility or network, embodiments of the disclosed method and system provide for receiving information from one or more systems and machines including the infusion pump administering sedation and pain therapy to the patient, the ventilator providing ventilation to the patient, hospital information system, monitors, laboratory systems and/or pharmacy and dispensing systems. In some embodiments, the information is collected directly from these devices without requiring any interaction from the nurse or therapist and used to generate analytics regarding the different steps of the rules and protocols regarding patient care, such as rules and protocols for ventilated patients with the goal of weaning a patient off of the ventilator. Other data, including, for example, demographic data regarding the patient as well as patient condition data, may also be collected and used to determine protocol and best practices compliance. In one example, in response to the information collected from the infusion pump and/or ventilator, and optionally other mechanisms or entities, one or more analytics may be generated. For example, compliance information may be generated that indicates whether the nurses and/or therapists are taking the right steps in optimal patient care. In one example, one or more markers and/or notifications may be provided to the nurse and/or therapist in response to the collected data.

In some examples, various rules and protocols for patient care may be generated for all patients. In one or more instances, rules and protocols may be customized and/or adjusted according to specific characteristics of patients, such that specific rules and protocols are provided for different collections of patients that may require specialized or customized care according to different circumstances, including the characteristics of the patients or the type of therapy being administered to the patient. Such characteristics may include care area, patient type, diagnosis-related group (DRG), or other categories defined based on patient characteristics. In one example, in addition to specific rules and/or protocols, various thresholds or markers may also be defined according to the type or patient or therapy and/or the determined patient category.

Measuring and driving compliance may enable clinicians to measurably optimize and improve the ventilator weaning of patients. The data collected can be processed to generate various markers and/or analytics that provide insight into the clinical intervention events and how the timing/pattern of these events affects the weaning process and facilitate a complete view of the weaning process, including sedation/pain therapy, SATs, SBTs and extubation, thus driving better cross-functional teamwork between physicians, nursing and respiratory technicians.

In various examples, the analytics data, including the one or more markers and/or notifications, may be correlated with patient outcome information to determine the impact of various protocols and/or best practices on patient outcome, and/or the impact of deviation from various protocols and/or best practices on patient outcome. In one example, the impact information may be used to modify protocols and/or best practices regarding patient care. Patient outcome information may be collected from various sources and may include information regarding patient weaning, discharge, readmission, or complications and/or long-term patient condition information. The outcome information for patients can be mapped to various markers indicating deviation from protocols and/or best practices to determine a weight or importance of various protocols and/or practices.

Figure 1B:
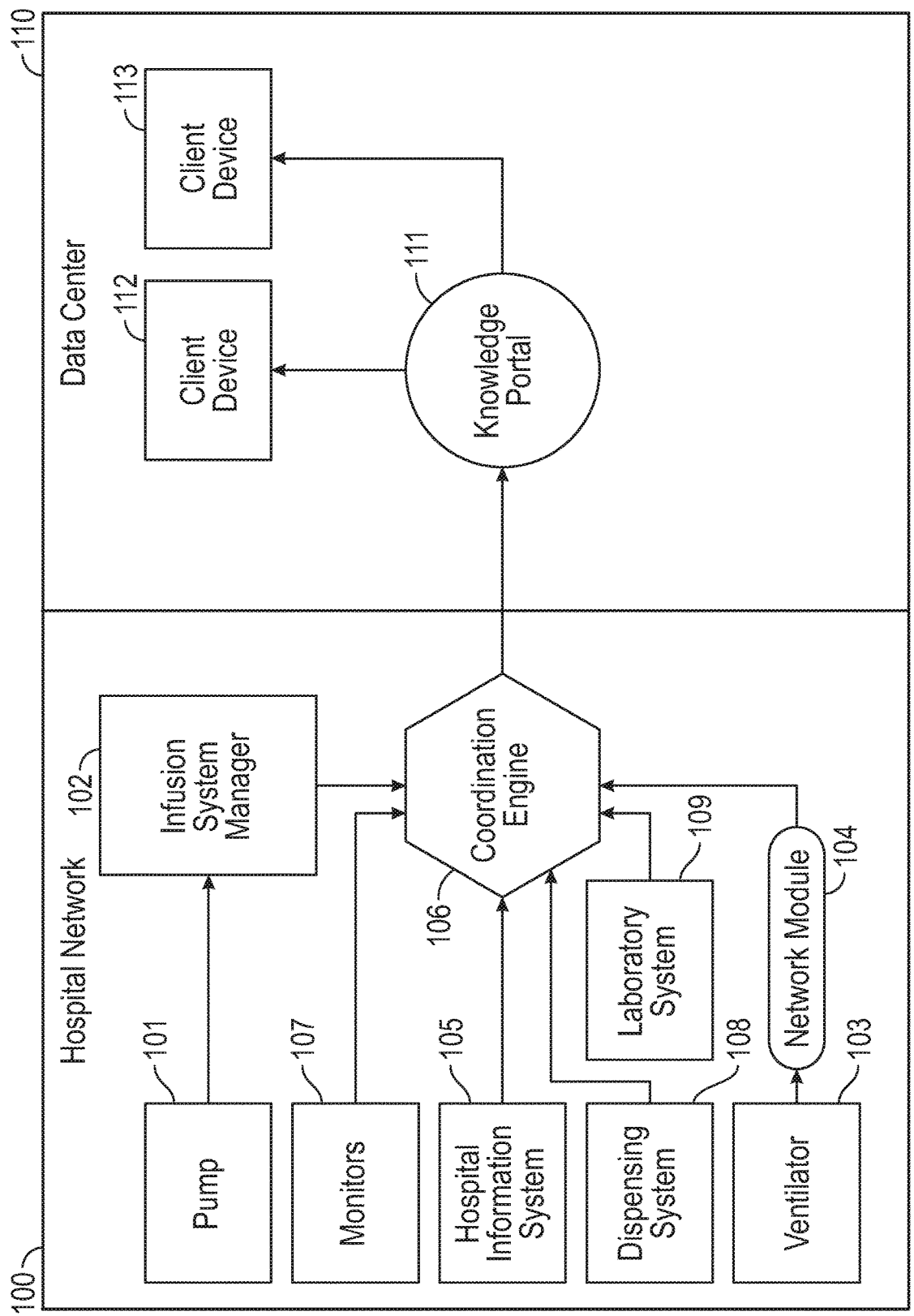

FIGS. 1A and 1B depict an example hospital network 100 for collecting patient information and facilitating management of rules and protocols for patients. As shown in FIG. 1A, the hospital network 100 includes an infusion pump 101, an infusion system manager 102, a ventilator 103, a network module 104, a hospital information system 105, and a coordination engine 106.

The infusion pump 101 provides sedation and pain therapy to a patient. In one example, the infusion pump 101 represents a collection of one or more infusion pumps for providing medication including pain and/or sedation medication to a patient. In one example, the infusion pump 101 may include one or more channels, and each channel may provide at least one of a sedative or pain medication (e.g., analgesics) to the patient. As described above, the infusion pump is typically operated by a nurse.

The infusion pump 101 is coupled to the infusion system manager 102 and provides infusion messages to the infusion system manager 102. The infusion messages may, for example, indicate start and end times for specific doses/rates of medication administered to the patient. For example, each time the dosage and/or rate of one or more of the medication (e.g., sedatives and/or analgesics) is modified at the pump 101, an infusion message is generated by the pump 101 and sent to the infusion system manager 102. In one example, the pump 101 provides messages regarding the type of medication, dosing of medication and bolus dose patterns of medication administered at the pump 101. The infusion system manager 102 may further receive information regarding the identification of the patient associated with infusion pump 101 from the pump 101 or hospital information system 105. The pump 101 and infusion system manager 102 are depicted as separate elements for exemplary purposes. In some embodiments, the functionality of the infusion system manager 102 may be integrated within infusion pump 101.

The infusion system manager 102 processes the infusion messages received from the pump 101 and provides infusion information to the coordination engine 106. In one example, the infusion information provided to the coordination engine 106 includes patient identification information (e.g., patient ID), drug information (e.g., drug type), infusion start and/or stop times for each drug, and dose and/or rates for each drug (e.g., continuous infusion dosage, bolus dosage patterns, etc.). The information may be provided for different drugs administered at pump 101, including the sedation and pain therapy medication administered to the patient. The ventilator 103 also provides information to the coordination engine 106 through the network module 104. Ventilation information provided to the coordination engine 106 may include the mode of ventilation, respiratory rate, tidal volume, amount of oxygen, amount of peek respiratory pressure, alarms that are triggered, and/or other ventilation information available at the ventilator 103. In one example, the ventilator 103 may further provide a respiratory rate over tidal volume calculation. The calculation may be the respiratory rate, which represents the number of breaths taken within a set amount of time (e.g., 60 seconds) over the tidal volume, which represents the normal volume of air displaced between normal respiration and expiration when extra effort is not applied. The information from the ventilator 103 is provided to the coordination engine 106 through network module 104. In some examples, the network module 104 may be integrated into the ventilator 103. In one embodiment, the ventilator 103, the network module 104 or a separate element in communication with the ventilator 103 and/or network module 104 may be present within the hospital network and configured to receive and/or process messages from the ventilator 103 before forwarding ventilation information to the coordination engine 106.

The coordination engine 106 may also receive patient "ADT information" from the hospital information system 105. The ADT (admission, discharge, transfer) information may include demographic information as well as patient state information. Patient demographic information may include, for example, patient sex, date of birth, attending, admitting and consulting doctors, location, blood type, height and weight, admit date and time, In/Out patient. Patient state information may include, for example, patient admit, discharge, transfer, registration, information update and other similar information regarding the state of the patient within the care facility.

In one embodiment, coordination engine 106 is embodied in any interface engine or application that aggregates data from one or more devices and systems and sends such data to an analytics application such as the knowledge portal 111. In one example, the coordination engine 106 facilitates processing, filtering and/or transformation of information received from one or more machines and/or systems including the infusion system manager 102 and network module 104, for facilitating transferring of the data to a respiratory knowledge portal 111 for processing and analysis. In one example, the coordination engine 106 receives the information, processes the information, and generates actionable data items for processing to the knowledge portal 111. In one embodiment, the coordination engine 106 is embodied in a processor. U.S. patent application Ser. No. 13/421,776, entitled "SCALABLE COMMUNICATION SYSTEM," filed on Mar. 15, 2012, filed on Jan. 31, 2013 and incorporated herein by reference in its entirety, describes an example coordination engine for use with the present disclosure.

The coordination engine 106 is communicably coupled to a respiratory knowledge portal 111 of a data center 110. Data center 110 includes the knowledge portal 110 communicably coupled to one or more client devices 112 and 113. The data center 110 may be located remote from the hospital network 100 or may be part of the hospital network 100. In one example, the coordination engine 106 and knowledge portal 111 may be implemented within a single server or one or more servers communicably coupled to one another. In some examples, the functionalities of the coordination engine 106 and knowledge portal 111 may be performed by a single application or one or more applications collaborating to performing one or more of the functionalities described herein with respect to the coordination engine 105 and knowledge portal 111.

In one example, the knowledge portal 111 receives the infusion information and ventilation information from the coordination engine 106, and processes the information to generate one or more markers and analytics and provide information regarding compliance with patient care rules and protocols. In some examples, the knowledge portal 111 may also compare the patient care compliance information with patient outcome information (e.g., ADT information, long term patient condition information, re-admittance information, etc.) to determine outcome correlations with various rules and protocols. The correlation information may be used to determine various modifications or enhancements to the patient care rules and protocols and/or to flag various rules and/or protocols as important depending on the impact of the compliance on patient outcome.

The knowledge portal 111, in some embodiments, is implemented as an application that receives information from one or more devices, such as pump 102 and ventilator 104, within a hospital network 100, and analyzes the data to provide analytics. In one embodiment, the respiratory knowledge portal 111 is embodied in a processor. U.S. patent application Ser. No. 13/756,421 entitled "RESPIRATORY KNOWLEDGE PORTAL," filed on Jan. 31, 2013 and incorporated herein by reference in its entirety, describes an example respiratory knowledge portal for use with the present disclosure.

The knowledge portal 111 may, for example, have access to a set of pre-defined rules and protocols (e.g., best practices). The rules and protocols may be defined based on historical data and/or manually by the care facility or other entity. In one example, the rules and protocols may be defined based on specific patient groups or characteristics. Using the infusion information and/or ventilation information received from the coordination engine 106, the knowledge portal 111 can determine one or more markers corresponding to preferences defined by the rules and protocols. The knowledge portal 111 may further be configured to measure variability from the pre-defined rules and protocols and may provide one or more analytics regarding the variance from rules and protocols (e.g., reports, notifications, etc.) to one or more entities (e.g., care facility supervisors, nurse, respiratory therapist, etc.).

In one example, a library (e.g., a drug library) is accessible by the knowledge portal 111. The drug library may include a master drug list that identifies drugs by name and/or an identifier. In one example, the knowledge portal 111 may further be configured with information regarding the drug type for drugs listed within the master list. For example, for one or more drugs of the master list, the knowledge portal 111 may have access to data identifying the drug type as a pain therapy drug (e.g., analgesics) or a sedative. In one example, the designation of drug types is performed by an entity such as the care facility or other third party entity.

As part of the rules and protocols, the knowledge portal 111 may further be provided with information indicating preferred drugs for a patient. In some examples, a preferred list of drugs may be provided. The preferred list of drugs may be defined in terms of individual drugs, drug combinations (e.g., a preferred pairing of drugs). The preferred drugs may be based on specific patients to whom the drug is being administered. For example, the rules and protocols may specify preferred pain therapy and sedative drugs for a patient. In other examples, the preferences may include a preferred dosage and/or dosage ratios for each of the pain therapy and sedatives. In some embodiments, the rules and protocols specify a preferred combination of pain therapy and sedation drugs. The combination of drugs may be specified to ensure the correct combination of specific drugs and/or dosing of those drugs.

Drug preferences may be defined based on patient specific characteristics, and defined per patient or for a group of patients sharing similar characteristics. In one example, a list of preferred medicine by patient type or therapy may be provided. Patient specific characteristics may include demographic information such as those examples provided herein. In some examples, as described above, patient groups may be defined by characteristics such as care area, patient type, DRG, or other similar characteristics. The knowledge portal may further have access to information regarding limits (e.g., hard and soft limits) for one or more drugs listed in the master list. In one example, the library includes drug information for each drug including the drug name and identifier, drug type and/or drug limits. In some examples, the drug library may further include information regarding the drugs, including for example, drug half-life, which refers to the duration of effectiveness of the drug (e.g., the duration before the drugs wears off).

Furthermore, the rules and protocols may include weaning rules and protocols, defining preferences regarding SATs and SBTs including timing, frequency and/or duration of SATs and SBTs, prerequisites to SBTs such as performing an SAT within a predefined period of time, and other patient data that may indicate whether the patient is a good candidate for an SBT and/or weaning (e.g., patient vitals, successful SATs, etc.), and/or rules regarding extubation, including timing of extubation and/or prerequisites such as a successful SBT performed within a specific period of time from the extubation and other patient data that may indicate whether the patient is a good candidate for an SBT and/or weaning (e.g., patient vitals, etc.).

Based on the defined rules and protocols and the information available regarding drugs within the master list, and the infusion information and ventilation information received from the coordination engine 106, the knowledge portal 111 may determine infusion and ventilation analytics. The infusion and ventilation analytics may provide insight regarding variance from the pre-defined rules and protocols.

FIG. 1B depicts an alternative example hospital network 100 for collecting patient information and facilitating management of rules and protocols for patients. The hospital network 100 of FIG. 1B is similar to that of FIG. 1A, but depicts additional systems and machines that may provide information used in addition to the infusion information and ventilation information, in generating the analytics at the knowledge portal 111.

The coordination engine is further coupled to monitors 107 (e.g., vital signs monitors), dispensing system 108 (e.g., a pharmacy system and/or dispensing machine(s)), and laboratory system 109. The coordination engine receives information regarding patient medications, condition and vital signs, from one or more machines and/or systems including, but not limited to, for example, monitors 107, dispensing system 108, and laboratory system 109 (e.g., a pharmacy system). In one example, other information regarding the patient including neurological assessment information may also be provided at the knowledge portal 111. The vital signs and other data may be used by the knowledge portal 111 in various steps of the processes described herein for determining analytics regarding variance from rules and protocols defining best practices, as well as to provide indicators of when a patient is a good candidate for weaning (e.g., one or more of an SBT or extubation) in addition to various markers and analytics described herein.

In one example, the knowledge portal 111 is coupled to the client devices 112 and 113 and provides the determined metrics and analytics for display at the one or more client devices 112 and 113. In one example, the metrics and analytics may be provided as notifications or warnings to nurses, respiratory technicians or other care providers (e.g., when a deviation from preferred rules and protocols is recognized, or when a preferred event should be performed). In another example, one or more of the markers and analytics may be provided to those in a supervisory role to provide an overall view of the process, identify issues in actual weaning processes and patient care, and provide insight into the pattern of events that lead to optimal results with respect to a patient. The metrics and analytics may be analyzed and provided in real time or near real time for display at the client devices 112 and 113. In one example, the analytics may further be used to provide decision support for performing patient care within respect to patients. In some embodiments, the knowledge portal 111 may provide the metrics and analytics to the client devices 112 and 113 over a wired or wireless network or communication channel.

In addition to the infusion information and ventilation information, the analytics generated at the knowledge portal 111 may further be generated based on other machine data providing patient information and vital signs, from one or more machines and/or systems including, but not limited to, for example, monitors 107, dispensing system 108 (e.g., a pharmacy system and/or dispensing machine(s)), and laboratory system 109. The vital signs and other data may be used by the knowledge portal 111 in various steps of the processes described herein for determining analytics regarding variance from rules and protocols defining best practices, as well as, to provide indicators of when a patient is a good candidate for weaning (e.g., one or more of an SBT or extubation) in addition to various markers and analytics described herein.

Figure 2:
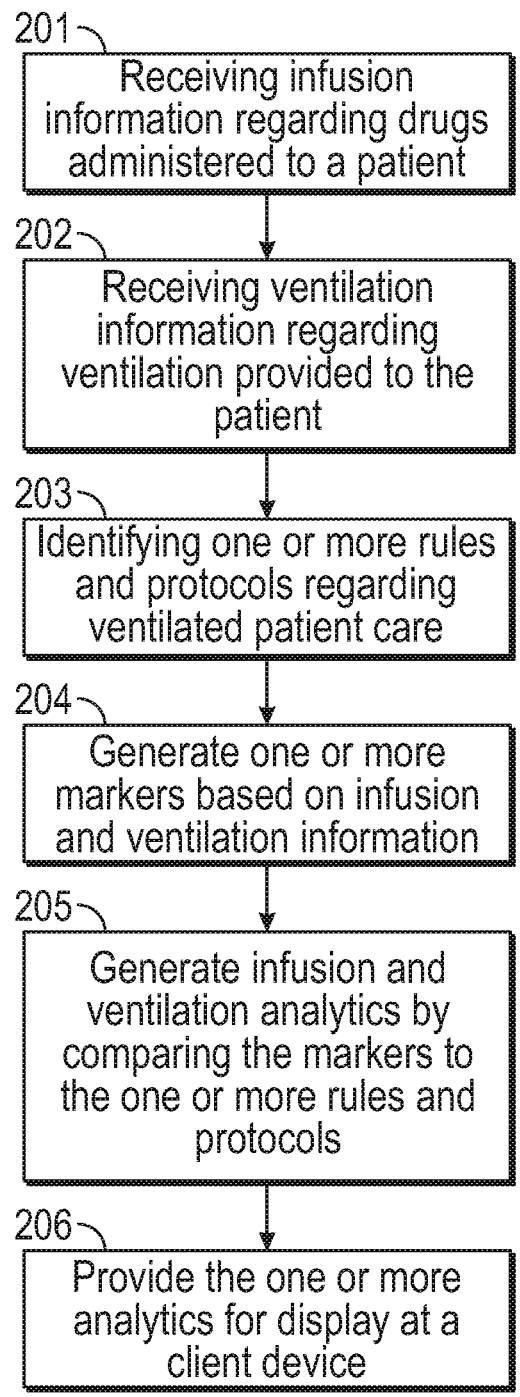
FIG. 2 illustrates an example process for providing information regarding compliance with patient care rules and protocols.

FIG. 2 illustrates an example process 200 for providing information regarding compliance with patient care rules and protocols. In one example, the patient may be a ventilated patient, however, various steps of the process may also be performed with other patients, including patients not requiring ventilation care. In step 201, infusion information regarding drugs administered to a patient is received at the knowledge portal 111. The information may be provided from an infusion pump (e.g., infusion pump 101 and/or infusion system manager 103). The information may include patient identification, drug types administered to a patient, drugs dosage and/or rates, as well as infusion start, stop.

In step 202, ventilation information regarding ventilation provided to the patient is received at the knowledge portal 111. The information may be received from a ventilator (e.g., ventilator 103). The information may include the mode of ventilation, respiratory rate, tidal volume, respiratory rate divided by the tidal volume, percent of inspired oxygen (e.g., within a range of 21% to 100%), amount of peek inspiratory pressure, alarms that are triggered, and/or or other ventilation information available at the ventilator. In other embodiments, information is provided from additional systems, as discussed above.

In step 203, one or more rules and protocols regarding patient care are identified. In one example, the rules and protocols define best practices for weaning patients off of mechanical ventilation. The rules and protocols may be pre-defined by an entity such as the care-facility or other entity having knowledge of best practices.

The rules and protocols identified in step 203 may, for example, include rules and protocols regarding medication or drugs administered to patients. In one example, the information indicates preferred drugs for a patient. For example, the rules and protocols may specify preferred pain therapy and sedative drugs for a patient as well as a preferred dosage and/or dosage ratios (e.g., ratio of sedative or pain therapy drugs for each patient) for such drugs. The rules and protocols may further include limits (e.g., soft or hard limits) for one or more drugs administered to a patient. Furthermore, the rules and protocols may include weaning rules and protocols, including rules and protocols regarding SATs, SBTs, and extubation including timing, frequency, duration and/or preceding or following events.

In step 204, one or more markers are calculated according to the information received in steps 201 and/or 202. In some embodiments, the one or more markers may also be generated based on information received from the hospital information system 105, monitors 107, dispensing system 108 and laboratory system 109. The one or more markers may correspond to desirable values and events defined by the rules and protocols identified in step 203. The one or more markers may, for example, include identification of the drugs administered to a patient, weight-based doses of drugs administered to a patient, information regarding bolus doses, and occurrence and timing of one or more SATs, SBTs and extubation.

In step 205 infusion and/or ventilation analytics are generated by comparing the one or more markers to the rules and protocols to determine a variance from best practices. For example, the drugs administered to a patient as well as the dosages of the drugs are compared to the rules and protocols to determine if the preferred drugs are administered to a patient at the preferred dosages, and within predefined limits. In one example, as described above, a list of preferred drugs may be provided (e.g., by patient type or therapy). The drugs administered to the patient may be compared against the list of preferred drugs to determine if preferred drugs are being administered to the patient. In one example, the dosage information regarding drugs being administered to the patient is further determined and compared to threshold values to determine if the correct dosage of the medication is being administered to the patient.

Furthermore, in some examples, it is determined whether SATs are administered according to best practice, including timing and frequency of SATs, and whether the SATs are successful based on at least the duration of each SAT. Additionally, in some examples, it is determined whether SBTs are performed according to the rules and protocols, including whether a patient that is a good candidate for weaning undergoes an SBT and whether prerequisites for an SBT are met, as well as the success of the SBT. Also, it may be determined if extubation of a patient is performed according to the rules and protocols including the timing of the extubation and prerequisites of the extubation being met. An example process for generating infusion analytics is described in further detail below with respect to FIG. 3. An example process for generating ventilation analytics is described in further detail below with respect to FIG. 4.

In step 206, the one or more analytics are provided for display at a client device. In one example, the analytics are provided as notifications to one or more entities such as a nurse or respiratory therapist. In another example, the analytics may be provided in one or more reports to one or more users in a supervisory role.

Figure 3:
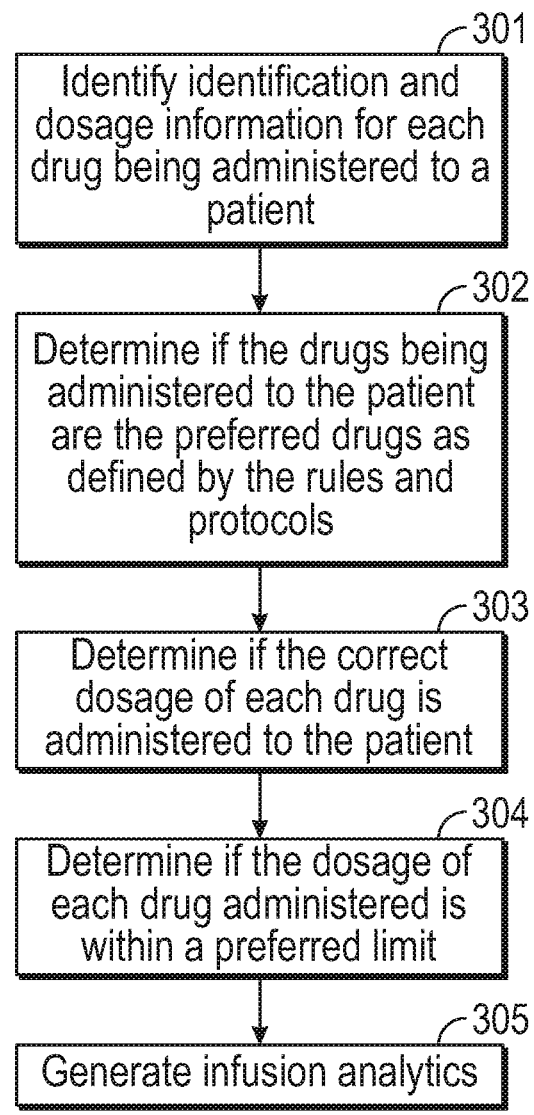
FIG. 3 illustrates an example process for generating example infusion analytics for a patient.

FIG. 3 illustrates an example process 300 for generating example infusion analytics for a patient.

In step 301, identification and dosage information for each drug administered to the patient are identified. As described above, with respect to FIG. 2, the identification and dosage information is determined based on information provided by the infusion pump. In one example, a drug library including a master drug list is used to identify drugs by name and/or an identifier. The infusion pump 101 provides the drug name and/or identifier for each drug administered to the patient at the infusion pump 101. Dosage information of the drug may be a weight based dosage of each drug administered to the patient calculated according to the dosage information for each drug administered as provided by the infusion pump, and a weight of the patient that is provided as part of the ADT information regarding the patient. In one example, the dosage information may include a dosage amount of the drug administered at a certain time or in a given period of time, or a cumulative dosage. In some example, the dosage amount may be determined based on scheduled dosage and/or bolus dosages being administered to the patient (e.g., over a period of time).

In step 302, it is determined if the drugs administered to the patient are the preferred drugs as defined by the rules and protocols. In one example, the rules and protocols define specific preferred sedative and pain therapy drugs to be administered to the patient. For example, the rules and protocols may specify preferred pain therapy and sedative drugs for a ventilator patient. In one example, the preferences may be defined according to specific patient characteristics (e.g., patient type or therapy type). The determination of which drugs are defined as preferred drugs for the patient may be performed by determining specific patient characteristics of the patient and determining the preferred drugs for the patient based on the characteristics.

In step 303, it is determined if the correct dosage of each drug is administered. The rules and protocols may specify preferred dosage and/or dosage ratios for the pain therapy and sedative drugs for a ventilator patient. In one example, the weight based dosages for each drug as identified in step 301 are used to determine if the dosage of each drug meets the defined dosage preferences. Bolus doses may also be analyzed to determine if the patient is being over medicated.

A dosage ratio may be calculated based on the weight based dosages of the sedative and pain therapy medications. In one example, the ratio defines a relationship between the amount (dosage) of a sedative administered to a patient and the amount (dosage) of a pain therapy drug administered to the patient. The calculated dosage ratio is then compared to the preferred dosage ratio as defined by the rules and protocols to determine if there is a variance between the calculated dosage ratio and the preferred dosage ratio.

In step 304, it is determined if the dosage of drugs administered is within a pre-defined limit. For example, information regarding limits (e.g., soft or hard limits) for one or more drugs may be accessed and compared to the dosages for each drug to determine if the dosages are within the limits for that drug.

Figure 5:
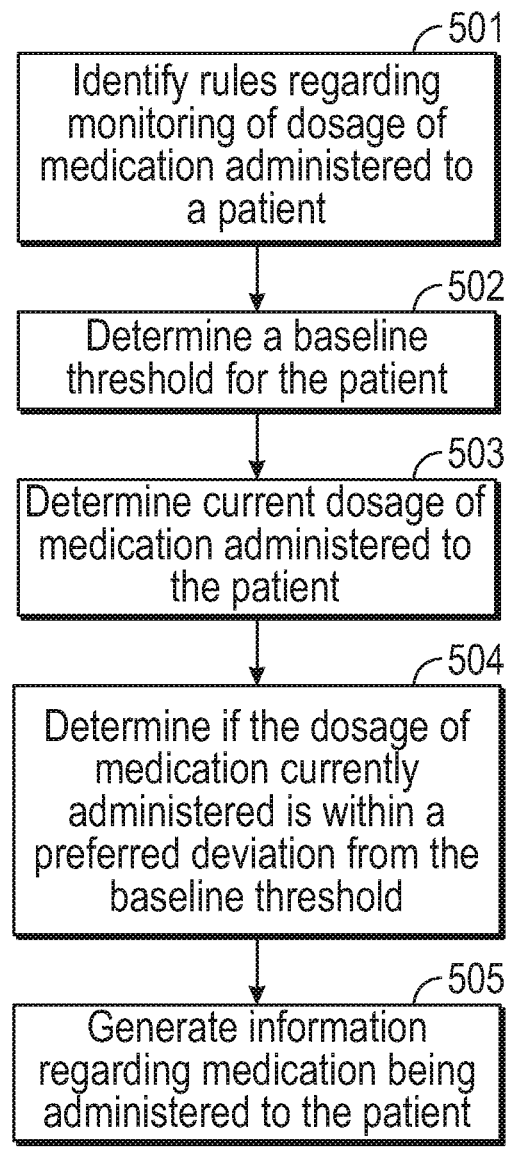
FIG. 5 illustrates an example process for determining if the dosage of drugs being administered to a patient complies with pre-defined rules and protocols.

In another example, the determination may be based on a baseline threshold calculated for the specific patient (or a group of patients). In one example, the baseline threshold may be determined according to the patterns of dosages administered to the patient (or other similar patients), for example, over a period of time. The identified dosages in step 301 may be compared to the baseline threshold to determine if the dosage administered is a proper dosage. FIG. 5, described in more detail below, illustrates an example process for determining if the dosage of drugs being administered to a patient complies with pre-defined rules and protocols.

As described above, the limits and thresholds for drugs dosages may be defined according to various patient characteristics. In one example, the patient may be determined to be within a category of patients according to various criteria (e.g., patient and therapy characteristics), and the rules and protocols, including preferred drugs, limits, thresholds, and other compliance information for the patient may be determined based on the patient category.

In one example, the drug limits, thresholds, rules and/or protocols may be determined and/or modified according to the drug type and/or drug half-life information. In one example, each drug may be associated with a half-life, and one or more rules and protocols, limits, thresholds, or measurements may be modified according to the half-life information of a drug being administered to the patient. As described above, half-life information indicates an effective duration for a drug. In one example, timing of various rules and protocols (e.g., when the drugs should be administered, when the patient should be taken off of drugs and/or ventilation, etc.) may be modified according to the half-life information.

In step 305, infusion analytics are generated according to the determinations in step 302, 303 and 304.

In one example, the analytics may be provided for display to one or more nurses, or supervisory personnel. In some examples, the analytics may be correlated with patient outcome information to determine a correlation between specific infusion practices and patient outcomes.

Figure 4:
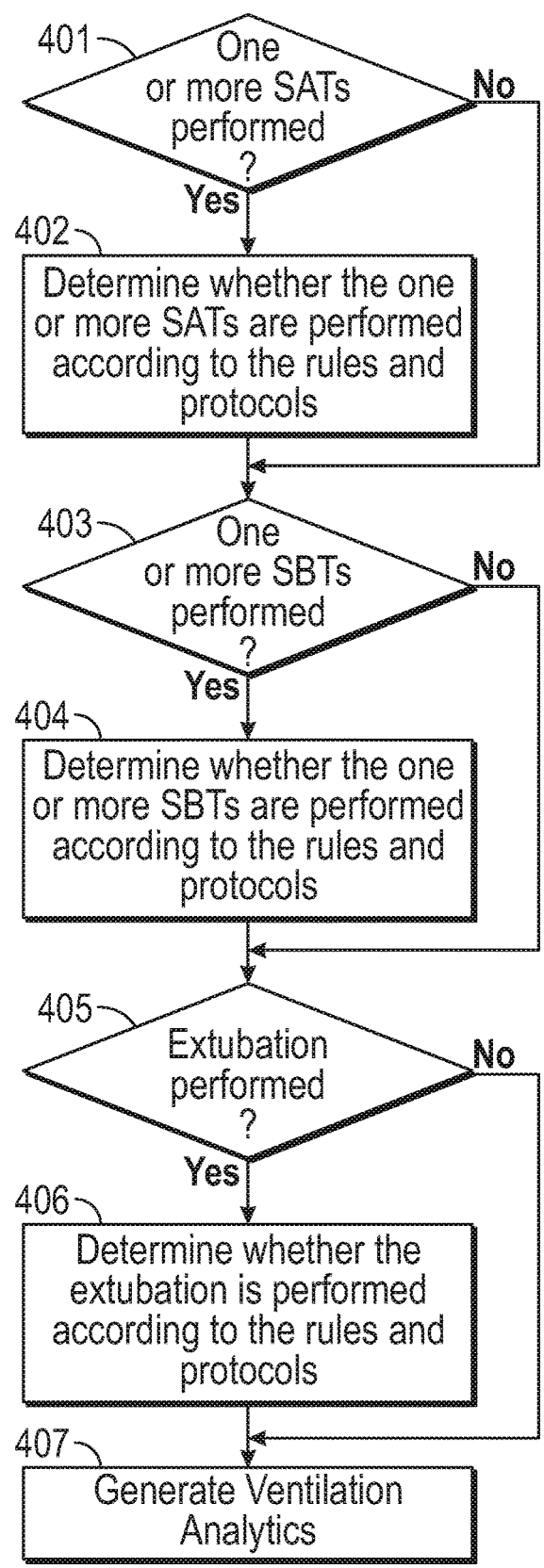
FIG. 4 illustrates an example process for generating example ventilation analytics for a patient.

FIG. 4 illustrates an example process 400 for generating example ventilation analytics for a patient.

In step 401 it is determined whether one or more SATs were performed with respect to the patient. In order to perform SATs or sedation vacations, the dosage of sedation and pain therapy medication administrated to a patient is typically reduced (e.g., to a lower dosage or stopped). In step 401, dosage information and infusion starts and stops provided by the infusion pump 101 to the coordinated engine 106 and knowledge portal 111 are analyzed to identify SATs. That is, changes in dosage and/or start/stop of dosage are analyzed and where the dosage is reduced to a level that indicates an SAT (e.g., reduced or stopped), a marker is generated indicating a start of an SAT. The dosages following the marker are then analyzed until an increase in dosage to a level indicating a termination of an SAT is observed (e.g., an increase or restart). Another marker is then generated indicating a termination of the SAT. Instead of a dosage increase, indicating a termination of an SAT, in some instances an SAT may be followed by an SBT. In such instances, a marker may be generated once an SBT is initiated, to indicate the termination of an SAT.

If, in step 401, one or more SATs are identified, in step 402, it is determined whether the SATs are performed according to the rules and protocols. For example, the rules and protocols may define preferred timing, frequency and/or duration of SATs. For example, the rules and protocols may define that SATs should be performed one or more times per day and/or preferred times for conducting SATs. The markers for the SATs are used to determine the frequency of the SATs and/or the timing for each SAT performed. The determined frequency and/or timing is then compared to the frequency and/or timing defined by the rules to determine if there is a variance between the frequency and/or timing actual of the performed SATs and the preferred frequency and/or timing of SATs.

Furthermore, the rules and protocols may define a preferred duration. The start/end markers for each SAT may be used to determine the duration of the SAT. The duration is then compared to the defined preferred duration. In one example, the preferred duration indicates that an SAT was successful. If, in step 401, no SATs are identified, the process continues to step 403.

As described above, rules and protocols regarding SATs may be determined and/or adjusted according to various criteria including for example, the specific characteristics of a patient or therapy being administered to the patient (e.g., patient category) and/or specific drugs being administered to the patient (e.g., drug half-life information). For example, the timing and/or duration of an SAT may be adjusted depending on the specific type of patient or the type of therapy. Similarly, the timing and/or duration of the SAT may be adjusted according to the specific type of drugs being administered to the patient. For example, the half-life information regarding the drug may be used to determine the appropriate timing/duration for an SAT based on the effective period of pain therapy and sedatives administered to the patient.

In step 403, it is determined whether one or more SBTs were performed with respect to the patient. When performing an SBT, the ventilator 103 is put into a different mode in order to perform the SBT. The mode information provided by the ventilator 103 is analyzed to determine when a change in mode indicative of an SBT occurs. A marker is generated when such a change is detected, marking the beginning of the SBT. Next, ventilator information is analyzed to identify a termination of the SBT. A termination of an SBT may be indicated by a change in the mode of the ventilator 103 or by the termination of ventilation indicative of an extubation. A marker is generated when an SBT termination is identified.

If, in step 403, one or more SBTs are identified, in step 404, it is determined whether the SBTs are performed according to the rules and protocols. In one example, the rules and protocols may include rules regarding preferred timing, frequency and/or duration of SATs. Furthermore, the rules may indicate one or more prerequisites before the SBT is performed.

For example, the rules may define that once it is determined that a patient is a good candidate for a SBT (e.g., a candidate for weaning), an SAT should be performed and after a predefined amount of time an SBT should be initiated. The markers for the SBT are used to determine the timing and duration of the SBT. Furthermore, the marker for the preceding SAT is used to determine the amount of time before an SBT is initiated following the SAT, and whether the SBT is successfully completed.

The rules and protocols may also define a preferred duration for an SBT. The start/end markers for each SBT may be used to determine the duration of the SBT. The duration is then compared to the defined preferred duration. In one example, the preferred duration indicates that an SBT was successful.

Furthermore, a successful SBT (e.g., defined by a specific duration) in patients that are good candidates for weaning should be followed by an extubation within a predefined amount of time of the SBT being initiated. The markers are used along with markers indicating an extubation to determine a time elapsed between a successful SBT and extubation in certain patients.

The information is then compared to the SBT rules and protocols to determine if there is a variance between the timing, duration and prerequisite of actual SBTs performed and the preferred timing, duration and prerequisite of SBTs. If, in step 403, no SATs are identified, the process continues to step 405.

In various implementations, rules and protocols regarding SBTs may be determined and/or adjusted according to various criteria including for example, the specific characteristics of a patient (e.g., patient category) and/or specific drugs being administered to the patient (e.g., drug half-life information). For example, the timing and/or duration of an SBT may be adjusted depending on the specific type of patient or the type of therapy. Similarly, the timing and/or duration of the SBT may be adjusted according to the specific type of drugs being administered to the patient. For example, the half-life information regarding the drug may be used to determine the appropriate timing/duration for an SBT based on the effective period of pain therapy and sedatives administered to the patient.

In step 405, it is determined whether an extubation of the patient was performed. An extubation may be identified if a termination in ventilation information is detected (e.g., following a successful SBT). In one example, in response to detecting a termination of ventilation information, a marker is generated indicating an extubation. In one example, a threshold time may be defined before a termination of ventilation is interpreted as an extubation. The threshold time may, for example, account for switching the patient to a remote ventilator for various reasons.

If, in step 405, it is determined that an extubation was performed with respect to the patient, in step 406 it is determined if the extubation was performed according to the rules and protocols. For example, the rules and protocols may define a timing for performing an extubation following a successful SBT being performed. The markers for SBTs and the extubation may be used to determine if an SBT was successfully completed and the time lapsed after the successful SBT (e.g., as defined by a specific duration), before extubation was performed. This information is then compared to the rules and protocols to determine if there is a variance between the timing and preceding events of the extubation and the defined rules and protocols for extubation.

In step 407, ventilation analytics are generated according to the determinations in steps 401-406.

Accordingly, the embodiments of the disclosed system and methods provide for processing information from one or more infusion pumps, ventilators, hospital information systems, monitors, dispensing systems, and/or laboratory systems providing information regarding a ventilated patient and analyzing the information to assess protocol and best practices compliance. The collected information can be processed to generate various markers and/or analytics that provide insight into the clinical intervention events and how the timing/pattern of these events affects the weaning process and facilitate a complete view of the weaning process, including sedation/pain therapy, SATs, SBTs and extubation, thus, driving better cross-functional team work between physicians, nursing and respiratory technicians. Measuring and driving compliance may enable clinicians to measurably optimize and improve the weaning of ventilated patients. Furthermore, the generated markers and analytics may help provide insight into how patient outcome relates to actual patient outcomes.

In one example, the analytics are compared against outcome information for the patient to determine how certain activity (e.g., following or deviating from certain rules and protocols, specific types of medication, or specific series of activity regarding patient care) relates to specific outcomes for patients. The correlation may occur for specific types of patients (e.g., based on patient category and characteristics), or based on specific types of therapy being provided to patients. The comparison may provide specific outcome analytics that provide insight as to the effectiveness of various practices in patient care.

In one example, the outcome information may be used to adjust various rules and protocols to achieve optimal results. In another example, the outcome information may be used to modify or adjust various thresholds, limits and criteria used to determine various analytics discussed herein. In one example, the outcome information may also be used to determine certain preferences including for example preferred drugs that lead to optimal results for certain patients, the preferences may be provided to the knowledge portal. In one example, thus, automatic generation and/or maintenance of rules and protocols is made possible through use of the analytics described herein.

FIG. 5 illustrates an example process 500 for determining if the dosage of drugs being administered to a patient complies with pre-defined rules and protocols.

In step 501, rules regarding medication dosage monitoring for a patient are identified. In one example, rules for monitoring medication dosage administration may be defined by a supervisory user (e.g., system administrator, care taking facility, etc.). In some examples, the rules may be defined at the time of configuring the system (e.g., knowledge portal) and may be updated according to various considerations (e.g., analytics and outcome information). In one example, the rules include an algorithm for determining a baseline threshold, time(s) for determining the baseline threshold, a threshold deviation from the baseline threshold, actions to be taken in the event of a deviation that meets and/or exceeds the baseline threshold, and other criteria or rules relating to monitoring of dosage of medication administered to a patient.

As described above, the rules may be patient or group specific based on a category of patients (e.g., patient or therapy type). In one example, the patient is identified and characteristics of the patient and/or the therapy administered to the patient are compared against the defined categories, and the patient is associated with a specific patient category. The rules regarding dosage monitoring may be identified for the user based on the patient category and/or patient and/or therapy characteristics.

In one or more examples, one or more of the rules, algorithms or values described for monitoring dosage administration may be defined in part based on the specific type of medication being administered to the patient. In one example, each drug may be identified and one or more values (e.g., threshold deviation, baseline threshold, etc.) may be identified and/or adjusted according to the specific identification of the medication. For example, as described above, in some examples, each medication may include half-life information and the rules identified in step 501 may be selected and/or adjusted according to half-life information of the medications being administered to the patient.

In step 502, a baseline threshold is determined for the patient. The baseline threshold may be determined according to the rules determined in step 501. In some examples, the baseline threshold may include one or more values indicating a normal amount of medication to be administered to the patient. In some examples, the baseline threshold may include a single value or a set of values. In one example, the baseline threshold may include a fixed value of the dosage of medication being administered to a patient at a specific period of time or over a period of time. In some examples, the baseline threshold may include a maximum and/or minimum dosages being administered to a patient over a period of time. In one example, the baseline threshold may include a rolling average of dosages of the medication being administered to a patient over a period of time.

In one example, the specific time or time period for determining the baseline threshold may be defined according to various criteria. In some examples, the baseline threshold may be defined as a dosage of each medication, or a dosage of all medications being administered to a patient. In some examples, the baseline threshold may include a cumulative dosage of medication (e.g., including regular and/or bolus dosages), a weight based dosage at a given time, or other dosage information indicating the actual medication administered to the patient.

In one example, a predefined set of rules may be established (e.g., at the time of configuring knowledge portal 111) that define the values (e.g., algorithms for calculating values) that make up the baseline threshold. In one example, the baseline threshold algorithm may be customized according to the patient type, category, specific drugs, or other characteristics of the patient, therapy or care taking facility.

In some examples, the specific time and/or time period used for determining the baseline threshold may be defined based on various criteria. For example, a fixed time or time period may be used. The fixed time period may represent a period of time that is most likely to provide a fair representation of the appropriate dosage of medications that should be administered to the patient. For example, time of day, number of possible interruptions (e.g., operations, visiting hours), or other considerations may result in a designation of a time period (e.g., a three hour window) which would provide the most optimal time for measuring a baseline dosage of medication being administered to the patient. In another example, a pattern may be defined for selecting the time or time segment (e.g., a pattern of a consecutive amount of time without interruption or with a fixed dosage within a predefined threshold).

In one example, the optimal time period and/or algorithm for determining the baseline threshold may be determined heuristically based on information provided from patients. For example, the dosages of medication administered to a specific patient, category of patients, or all patients may be obtained and analyzed to determine the optimal time period for determining the baseline threshold of dosages of medications to be administered to the patient. In one example, the patterns of drug administration, may, for example, be analyzed to determine the optimal time(s) for defining or determining the baseline threshold of the dosages to be administered to the patient. Similarly, algorithms used to determine the baseline threshold may be analyzed, for example, across various patients, category of patients, etc., to determine the optimal algorithms for calculating the baseline threshold, for one or more patients or groups of patients.

In step 503, dosage information including the dosage of medication currently being administered to the patient is determined. In one example, the dosage information may be the dosage of medication at a specific time or may be a cumulative dosage over a period of time. In one example, the dosage information may include bolus doses as well as continuous doses. In one example, the dosage information may be determined according to information received from the infusion pump 101. The infusion pump 101 provides the drug name and/or id for each drug administered to the patient at the infusion pump 101. Dosage information of the drug may be a weight based dosage of each drug administered to the patient calculated according to the dosage information for each drug administered as provided by the infusion pump, and a weight of the patient that is provided as part of the ADT information regarding the patient. In one example, the dosage information may include a dosage amount of the drug administered at a certain time or in a given period of time, or a cumulative dosage. In some examples, the dosage amount may be determined based on scheduled dosage and/or bolus dosages being administered to the patient (e.g., over a period of time).

In step 504, the dosage information is compared to the baseline threshold to determine if the dosage of medication being administered to the patient satisfies a condition with respect to the baseline threshold. In one example, the condition may include whether the actual dosage of medication being administered to the patient varies by a certain deviation threshold from the baseline threshold (e.g., one or more values including, for example, an overall rolling average for the day and/or a specific time segment maximum). The condition, in one example, may be defined according to the rules and protocols and may define a desired relationship with respect to a set of values defined by the baseline threshold.

In one example, the determination may generate a marker if there is a deviation from the baseline threshold by a defined deviation threshold (e.g., over dosage and/or under dosage). In one example, as described above, the determination may include a separate determination for each drug, or a combination one or more drugs (e.g., sedatives and/or analgesics) being administered to the patient. In one example, the deviation threshold may be expressed in terms of a fixed value, a percentage, and/or cumulative value. For example, the threshold deviation may be a specific amount of dosage over (or under) the baseline threshold. In another example, the threshold deviation may be expressed in terms of the percentage of the dosage being administered to the patient and/or a percentage of the baseline threshold. In some instances, the threshold deviation may be an amount of cumulative dosage in view of the baseline threshold. As described above, the threshold deviation may be defined according to the rules determined in step 501.

In some examples, the comparison may be performed with respect to a specific point in time or segment of time (e.g., a time period of 3 hours). In some examples, the time periods for the comparison and/or the frequency of the determination and comparison of process 500 may be defined according to the rules determined in step 501. In one example, the time periods and/or frequency may be adjusted according to the specific information or activity observed with respect to the patient (e.g., if a deviation is observed, the frequency of comparison may be increased and/or the time segment for comparison may be decreased).

In step 505, information regarding medication being administered to the patient is generated according to the comparison. In one example, the information includes one or more notifications and/or markers indicating the deviation from the normal or acceptable dosage of medication (e.g., as defined by the baseline threshold) administered to the patient. For example, a notification or marker is generated when the comparison indicates that the dosage of medication administered to a patient at a certain point in time or certain period of time is above a threshold deviation from the baseline threshold, which represents the normal dosage of medication that should be administered to the patient.

Figure 6:
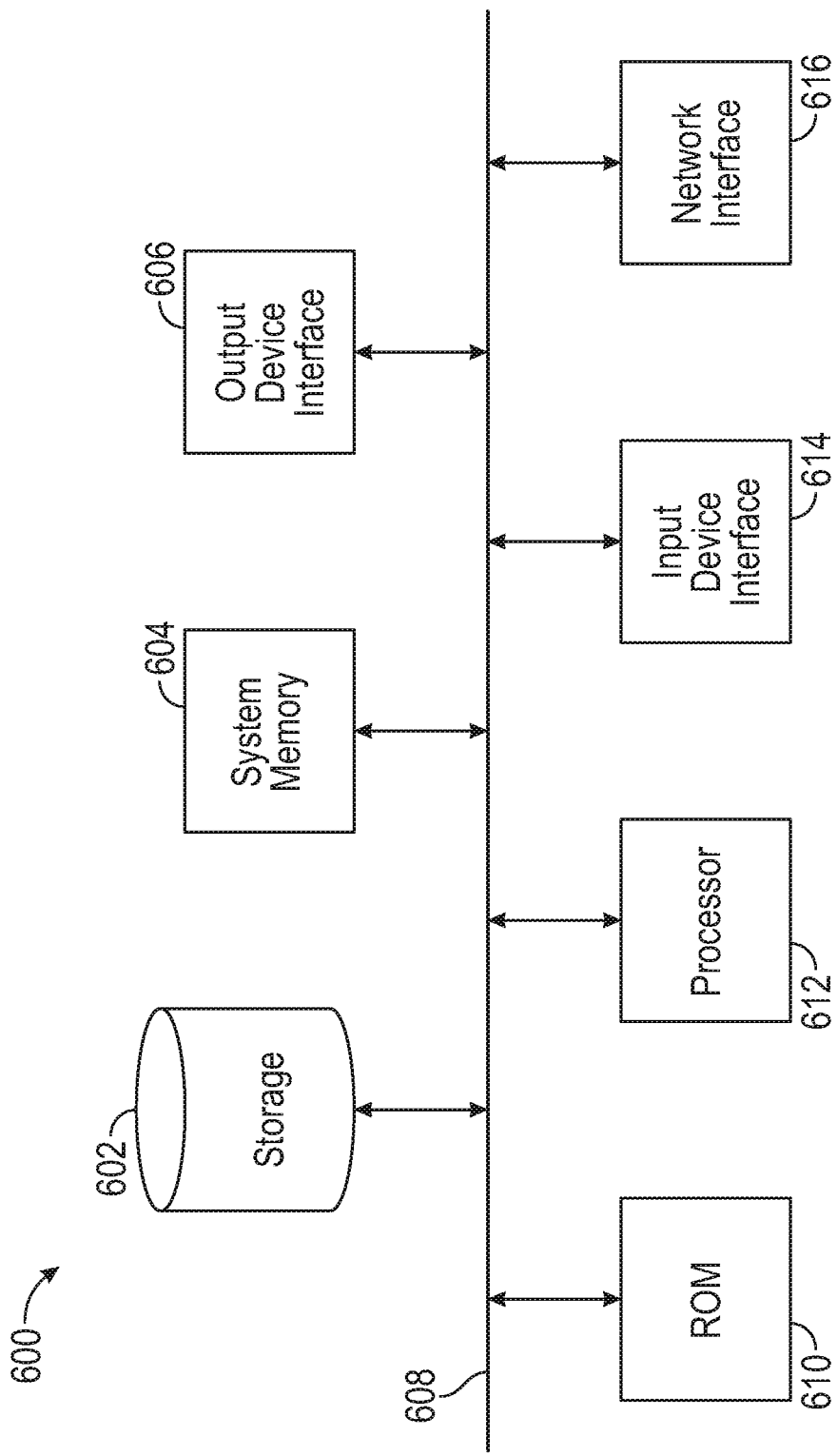
FIG. 6 conceptually illustrates an electronic system with which some implementations of the subject technology are implemented.

FIG. 6 conceptually illustrates an electronic system with which some implementations of the subject technology are implemented. Electronic system 600 can be a server, computer, phone, PDA, laptop, tablet computer, television with one or more processors embedded therein or coupled thereto, or any other sort of electronic device. Such an electronic system includes various types of computer readable media and interfaces for various other types of computer readable media. Electronic system 600 includes a bus 608, processing unit(s) 612, a system memory 604, a read-only memory (ROM) 610, a permanent storage device 602, an input device interface 614, an output device interface 606, and a network interface 616.

Bus 608 collectively represents all system, peripheral, and chipset buses that communicatively connect the numerous internal devices of electronic system 600. For instance, bus 608 communicatively connects processing unit(s) 612 with ROM 610, system memory 604, and permanent storage device 602.

From these various memory units, processing unit(s) 612 retrieves instructions to execute and data to process in order to execute the processes of the subject disclosure. The processing unit(s) can be a single processor or a multi-core processor in different implementations.

ROM 610 stores static data and instructions that are needed by processing unit(s) 612 and other modules of the electronic system. Permanent storage device 602, on the other hand, is a read-and-write memory device. This device is a non-volatile memory unit that stores instructions and data even when electronic system 600 is off. Some implementations of the subject disclosure use a mass-storage device (such as a magnetic or optical disk and its corresponding disk drive) as permanent storage device 602.

Other implementations use a removable storage device (such as a floppy disk, flash drive, and its corresponding disk drive) as permanent storage device 602. Like permanent storage device 602, system memory 604 is a read-and-write memory device. However, unlike storage device 602, system memory 604 is a volatile read-and-write memory, such a random access memory. System memory 604 stores some of the instructions and data that the processor needs at runtime. In some implementations, the processes of the subject disclosure are stored in system memory 604, permanent storage device 602, and/or ROM 610. For example, the various memory units include instructions for determining compliance with one or more patient care rules and protocols according to various implementations. From these various memory units, processing unit(s) 612 retrieves instructions to execute and data to process in order to execute the processes of some implementations.

Bus 608 also connects to input and output device interfaces 614 and 606. Input device interface 614 enables the user to communicate information and select commands to the electronic system. Input devices used with input device interface 614 include, for example, alphanumeric keyboards and pointing devices (also called "cursor control devices"). Output device interfaces 606 enables, for example, the display of images generated by the electronic system 600. Output devices used with output device interface 606 include, for example, printers and display devices, such as cathode ray tubes (CRT) or liquid crystal displays (LCD). Some implementations include devices such as a touchscreen that functions as both input and output devices.

Finally, as shown in FIG. 6, bus 608 also couples electronic system 600 to a network (not shown) through a network interface 616. In this manner, the computer can be a part of a network of computers (such as a local area network ("LAN"), a wide area network ("WAN"), or an Intranet, or a network of networks, such as the Internet. Any or all components of electronic system 600 can be used in conjunction with the subject disclosure.

These functions described above can be implemented in digital electronic circuitry, in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

In the previous detailed description, numerous specific details have been set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 36 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A machine-implemented method, comprising:

administering, by one or more infusion pumps, one or more medications to one or more ventilated patients;

reducing, during a plurality of time segments, a dosage of at least one of the one or more medications administered to a patient of the one or more ventilated patients;

receiving, by a processor, infusion information from the one or more infusion pumps and ventilation information from one or more ventilators associated with providing ventilation to the one or more ventilated patients, the infusion information indicating at least one infusion interruption experienced by the patient based on the reducing of the dosage during the plurality of time segments;

determining, by the processor, a pattern of a consecutive amount of time without interruption or with a fixed dosage within a predefined threshold for the time segments from the infusion information;

determining, by the processor, an optimal time segment based on the pattern;

calculating, by the processor, one or more baseline thresholds for the one or more medications for the patient, the one or more medications including sedatives and pain therapy drugs, the one or more baseline thresholds being calculated from one or more dosages of medications when previously administered to the patient or the one or more ventilated patients during one or more previous time segments corresponding to the determined optimal time segment;

periodically determining, in real time by the processor, a current dosage amount of the one or more medications currently being administered to the current-patient during a respective time segment by an infusion pump;

performing a periodic comparison, in real time by the processor while the patient is being administered the one or more medications by the infusion pump and while the patient is being ventilated by the ventilator, of the current dosage amount to the one or more baseline thresholds, the periodic comparison being performed at a predetermined frequency;

determining, by the processor based on the periodic comparing, a deviation in the current dosage amount that meets a threshold deviation from the one or more baseline thresholds;

in real time by the processor in response to the deviation:
generating a marker regarding administration of the one or more medications to the patient and relating to a ventilator weaning process for the patient,
providing, to a client device associated with a care giver and remote from the processor, a notification indicating the current dosage amount deviates from a normal or acceptable dosage of medication administered to the patient and indicating that an event should be performed, and increasing the frequency of the periodic comparison or decreasing the respective time segment for future determining of dosage amounts being administered to the patient;

determining, based on the generated marker and the infusion information and the ventilation information for the patient, to initiate termination of ventilation to the patient;

terminating the ventilation of the patient; and providing, to the client device, a notification regarding the terminating of the ventilation.

2. The method of claim 1, further comprising:

identifying a set of rules and protocols for monitoring patient care, the set of rules including an algorithm for determining the baseline thresholds and for determining a timing for terminating the ventilation, wherein the notification regarding the terminating the ventilation indicates whether the ventilation of the patient or terminating the ventilation was performed according to the set of rules and protocols.

3. The method of claim 2, further comprising:

updating patient outcome information associated with the one or more ventilated patients based on the marker; and updating the set of rules and protocols based on the updated patient outcome information.

4. The method of claim 2, further comprising:

identifying one or more characteristics of the patient; and identifying a patient category of the patient according to the characteristics, wherein the identifying the set of rules is based on the identified patient characteristics and patient category.

5. The method of claim 2, wherein the set of rules and protocols include a list of preferred medications for the patient.

6. The method of claim 5, further comprising:

comparing the medications currently being administered to the patient to the list of preferred medications to determine if each of the medications currently being administered to the patient is a preferred medication.

7. The method of claim 1, further comprising determining whether a preferred medication is being administered to the patient.

8. The method of claim 1, wherein each baseline threshold is one or more of a maximum, minimum or a rolling average of a dosage amount of the medications administered to the patient over the previous time segment corresponding to the determined optimal time segment.

9. The method of claim 8, wherein each baseline threshold is the rolling average of the dosage amount of the medications administered to the patient over the previous time segment corresponding to the determined optimal time segment.

10. The method of claim 1, wherein determining the current dosage amount of the medications comprises calculating a weight based dosage of each of the medications currently being administered to the patient based at least in part on infusion information and a weight of the patient.

11. The method of claim 10, wherein the current dosage amount of the medications comprises one or more of a continuous dosage and bolus dosage of each of the medications over the respective time segment.

12. The method of claim 1, wherein the current dosage amount of the medications is received from the one or more infusion pumps.

13. A system, comprising:
an infusion pump administering one or more medications to a patient and providing infusion information pertaining to the one or more medications being provided to the patient, wherein the one or more medications include a sedative or a pain therapy drug, the infusion pump reducing a dosage of at least one of the on or more medications administered to the patient during a plurality of time segments; and
a processor communicably coupled to the infusion pump and configured to:
  receive the infusion information from infusion pump and ventilation information from a ventilator associated with providing ventilation to the patient, the infusion information indicating at least one infusion interruption experienced by the patient based on the reducing of the dosage during the plurality of time segments;
  determine a pattern of a consecutive amount of time without interruption or with a fixed dosage within a predefined threshold for the time segments from the infusion information;
  determine an optimal time segment based on the pattern;
  calculate one or more baseline thresholds for the one or more medications for the patient, the baseline thresholds being calculated from one or more dosages of the one or more medications when previously administered to the patient or one or more additional patients during one or more previous time segments corresponding to the determined optimal time segment;
  periodically determine, in real time, a current dosage amount of the one or more medications currently being administered by the infusion pump to the patient during a respective time segment by an, infusion pump;
  perform a periodic comparison, in real time while the patient is being administered the one or more medications by the infusion pump and while the patient is being currently ventilated by the ventilator, the current dosage amount to the one or more baseline thresholds, the periodic comparison being performed at a predetermined frequency;
  determine, by the processor based on the periodic comparing, a deviation in the current dosage amount that meets a threshold deviation from the one or more baseline thresholds;
  in real time in response to the deviation:
    generate a marker regarding administration of the medications to the current patient and relating to a ventilator weaning process for the patient,
    provide, to a client device associated with a care giver and remote from the system, a notification indicating the current dosage amount deviates from a normal or acceptable dosage of medication administered to the patient and indicating that an event should be performed, and
    increase the frequency of the periodic comparison or decreasing the respective time segment for future determining of dosage amounts being administered to the patient;
  determining, based on the generated marker and the infusion information and ventilation information, to initiate termination of ventilation to the patient;
  facilitating terminating the ventilation of the patient; and
  providing, to the client device, a notification regarding the terminating of the ventilation.

14. The system of claim 13, wherein the processor is further configured to:
  identify a set of rules and protocols for monitoring patient care, the set of rules including an algorithm for determining each baseline threshold;
  update patient outcome information associated with the one or more ventilated patients based on the marker; and
  update the set of rules and protocols based on the updated patient outcome information.

15. The system of claim 14, wherein each baseline threshold is one or more of a maximum, minimum or a rolling average of a dosage amount of the medications administered to the patient over the previous time segment corresponding to the determined optimal time segment.

16. The system of claim 14, wherein the processor is further configured to:
  determine one or more characteristics of the patient;
  determine one or more characteristics of therapy being administered to the patient;
  determine a patient category of the patient according to the one or more characteristics of the patient and therapy; and
  identify the set of rules and protocols based on the determined patient category.

17. The system of claim 14, wherein the processor is further configured to:
  determine half-life information for each of the medications currently being administered to the patient; and
  modify one or more of the set of rules and protocols according to the half-life information.

18. The system of claim 13, wherein the processor is further configured to:
  determine a set of preferred drugs according to a set of rules and protocols;
  compare the one or more drugs being administered to the patient to the set of preferred drugs; and
  generate analytics including information regarding whether the one or more drugs administered to the patient are preferred drugs.

19. The system of claim 13, wherein the processor is further configured to:
  determine a set of patient outcome data for the current patient, the outcome data defining the outcome of patient care;
  correlate the outcome data to analytics regarding patient care generated for the patient; and
  generate analytics regarding an effect of a set of rules and protocols on the outcome of patient care for the patient.

20. A iron-transitory computer-readable medium having computer-executable instructions stored thereon for execution by a processor to perform a method, the method comprising:
  administering, by one or more infusion pumps, one or more medications to one or more ventilated patients;
  reducing, during a plurality of time segments, a dosage of at least one of the one or more medications administered to a patient of the one or more ventilated patients;
  receiving, infusion information from the one or more infusion pumps and ventilation information from one or more ventilators associated with providing ventilation to the one or more ventilated patients, the infusion information indicating at least one infusion interruption experienced by the patient based on the reducing of the dosage during the plurality of time segments;

determining a pattern of a consecutive amount of time without interruption or with a fixed dosage within a predefined threshold for the time segments from the infusion information;

determining an optimal time segment based on the pattern;

calculating one or more baseline thresholds for the one or more medications for the patient, the one or more medications including sedatives and pain therapy drugs, the one or more baseline thresholds being calculated from one or more dosages of medications when previously administered to the patient or the one or more ventilated patients during one or more previous time segments corresponding to the determined optimal time segment;

periodically determining, in real time, a current dosage amount of the medications currently being administered to the patient during a respective time segment by an infusion pump;

performing a periodic comparison, in real time while the patient is being administered the one or more medications by the infusion pump and while the patient is being currently ventilated by the ventilator, the current dosage amount to the one or more baseline thresholds, the periodic comparison being performed at a predetermined frequency;

determining, by the processor based on the periodic comparing, a deviation in the current dosage amount that meets a threshold deviation from the one or more baseline thresholds; and in real time by the processor in response to the deviation:
   generating a marker regarding administration of the one or more medications to the patient and relating to a ventilator weaning process for the patient,
   providing a notification of the generated marker to a client device remote from the processor, the notification indicating the current dosage amount deviates from a normal or acceptable dosage of medication administered to the patient, and
   increasing the frequency of the periodic comparison or decreasing the respective time segment for future determining of dosage amounts being administered to the patient;

determining, based on the generated marker and the infusion information and the ventilation information for the patient, to initiate termination of ventilation to the patient;

facilitating terminating the ventilation of the patient; and providing, to the client device, a notification regarding the terminating of the ventilation.

* * * * *

UNITED STATES PATENT AND TRADEMARK OFFICE
CERTIFICATE OF CORRECTION

PATENT NO. : 11,183,287 B2
APPLICATION NO. : 14/099773
DATED : November 23, 2021
INVENTOR(S) : Steinhauer et al.

Page 1 of 1

It is certified that error appears in the above-identified patent and that said Letters Patent is hereby corrected as shown below:

On the Title Page

Item (56) Under REFERENCES CITED:
Under U.S. PATENT DOCUMENTS:
Please change the name of the inventor for patent 4,551,133 from "Beyl" to --Zegers de Beyl et al.--.

Signed and Sealed this
Ninth Day of August, 2022

Katherine Kelly Vidal
*Director of the United States Patent and Trademark Office*